United States Patent [19]

Roomi

[11] 4,423,731
[45] Jan. 3, 1984

[54] SURGICAL DRESSINGS

[76] Inventor: Reyadh K. Roomi, Leicester General Hospital, Gwendolen Rd., Leicester, England

[21] Appl. No.: 299,498

[22] Filed: Sep. 4, 1981

[30] Foreign Application Priority Data

Sep. 9, 1980 [GB] United Kingdom ............... 8029082

[51] Int. Cl.³ ..................... A61B 17/04; A61B 17/08
[52] U.S. Cl. ................................ 128/335; 128/334 R
[58] Field of Search ............... 128/334 C, 334 R, 335

[56] References Cited

U.S. PATENT DOCUMENTS

| | | | |
|---|---|---|---|
| 114,750 | 5/1871 | Battersby | 128/335 |
| 363,538 | 5/1887 | Penny | 128/335 |
| 1,074,413 | 9/1913 | De Baum et al. | 128/335 |
| 1,969,188 | 8/1934 | Spicer | 128/335 |
| 2,196,296 | 4/1940 | Flynn | 128/335 |
| 2,303,131 | 11/1942 | Morgan | 128/335 |
| 2,387,131 | 10/1945 | Fernandez | 128/335 |
| 2,409,261 | 10/1946 | Dow | 128/335 |
| 2,751,909 | 6/1956 | Weitzner | 128/335 |
| 2,762,371 | 9/1956 | Guio | 128/335 |
| 3,698,395 | 10/1972 | Hasson | 128/335 |
| 3,926,193 | 12/1975 | Hasson | 128/335 |
| 3,971,384 | 7/1976 | Hasson | 128/335 |

Primary Examiner—C. Fred Rosenbaum
Assistant Examiner—C. W. Shedd
Attorney, Agent, or Firm—Spensley, Horn, Jubas & Lubitz

[57] ABSTRACT

The invention relates to a surgical dressing for use in closing incisions while healing, comprising at least two strips (2, 16) of adhesive plaster each adapted to lie alongside but slightly spaced from lengthwise extending edges of the wound, each plaster strip having secured therein at spaced intervals along its length end portions of a plurality of threads (4, 20) or filaments, each thread or filament of one adhesive strip being adapted in use to co-operate under tension with at least one thread or filament of an adhesive strip on the opposite side of the wound to draw the edges of the wound together, the length of the thread ($\propto$, 20) or filament extending from each strip (2, 16) being greater than the width of the strip itself.

The threads may either have free ends which may be tied or may be secured in a second plaster strip 22 which adheres to the skin at a region farther away from the wound.

3 Claims, 10 Drawing Figures

SURGICAL DRESSINGS

BACKGROUND OF INVENTION

The invention is concerned with improvements in or relating to surgical dressings, particularly surgical dressings for use in maintaining elongate slit-type wounds in a closed condition while healing takes place.

While slit wounds are commonly the result of surgery, it is intended that the term wound as used in this specification shall also cover any accidental wound of this kind which may have been inflicted by contact with a relatively sharp edge.

Although various attempts have been made to close this type of wound by surgical dressings, by far the most common method of closing is by suturing, that is the insertion of stitches which bridge the wound. This suturing process is painful, often requiring extended periods during which the patient is anaesthetised, often produces an inflamatory reaction and tends to leave unsightly scars, both from the stitch holes themselves and from the varying tension applied to the wound between the suturing points themselves and at intervening spaces. Moreover, a return visit to hospital is often necessary for the removal of stitches, whereas a surgical dressing may be readily removed by a nurse or the patient himself.

BRIEF DESCRIPTION OF INVENTION

It is therefore an object of the invention to provide an improved surgical dressing for use as an acceptable alternative to conventional suturing techniques.

The invention therefore provides a surgical dressing for use to maintain elongate slit-type wounds in a closed condition comprising at least two strips of adhesive plaster each adapted to lie alongside but slightly spaced from lengthwise extending edges of the wound, each plaster strip having secured therein at spaced intervals along its length end portions of a plurality of threads or filaments, each thread or filament of one adhesive strip being adapted in use to co-operate under tension with at least one thread or filament of an adhesive strip on the opposite side of the wound to draw the edges of the wound together, the length of the thread or filament extending from each strip being greater than the width of the strip itself.

It is important that the strips of adhesive plaster, by which is meant lengths of fabric or other material adapted to temporarily adhere to skin by means of a pressure-sensitive adhesive layer, are spaced slightly away from the wound so that the adhesion of the strips and therefore the tension of the threads or filaments is not diminished by the effect of seepage from the wound. Moreover, the progress of the healing of the wound may be readily inspected without disturbing the dressing.

In one of the examples of the invention to be described hereinafter, the dressing comprises two strips, each thread or filament extending from a first of the two strips having a free end suitable for tying with the free end of an appropriate thread or filament extending from a further strip situated on the opposite side of the wound. In this case, a method of applying the dressing to a wound includes the step of tying each thread or filament of the first strip to an appropriate thread or filament of the further strip with selected tension so as to draw the edges of the wound together progressively as each pair of threads or filaments are tied together with a tension appropriate to the requirements of the wound in the region of each tied pair of threads or filaments.

In another example of the invention, each thread or filament extending from a first of the strips is secured at its opposite end portion to a second of the strips to form a pair of first and second strips, one pair of first and second strips being associated with a second pair of first and second strips by the interlacing of the threads or filaments in an alternate manner.

A method of applying this example of a dressing according to the invention includes the step of applying tension to the interlaced threads or filaments by pulling upon said second strips thereby causing the first strips to move slightly together to close the wound, tension in the interlacing threads or filaments being maintained by causing the second strips of each pair of strips to adhere to the patient's skin at regions beyond the adhered first strips, so that each thread or filament spans the wound and completely traverses the first strip of the other pair of strips.

The strips may be rectangular in shape and therefore suitable for use with straightline wounds but many surgical incisions are curved to some extent and therefore the shape of the strips may be curved or otherwise nonrectilinear to permit use with variously shaped wounds.

BRIEF DESCRIPTION OF THE DRAWINGS

There will now be described two examples of surgical dressings according to the invention. It will be understood that the description, which is intended to be read with reference to the drawings, is given by way of example only and not by way of limitation.

In the drawings.

DETAILED DESCRIPTION OF THE DRAWINGS

Figure 1:
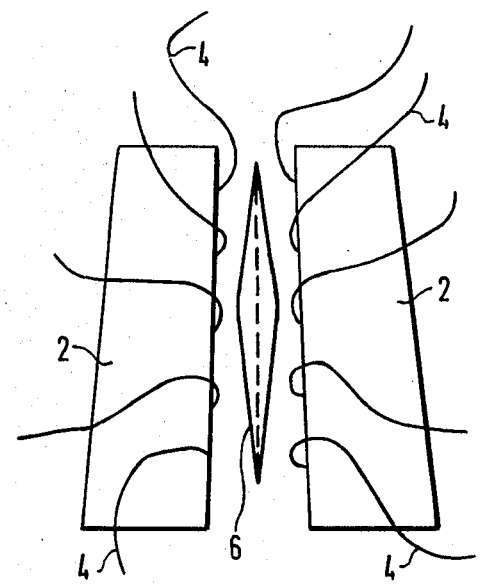
FIG. 1 illustrates in diagrammatic form a first example of a surgical dressing according to the invention.

FIG. 1 shows a surgical dressing comprising two strips of adhesive plaster 2, each strip being provided with a plurality, in the present example, five, of threads 4 extending from a lengthwise edge thereof. After removal of a conventional protective layer from the adhesive surface, each strip is positioned on an area of skin alongside but spaced from a gaping, elongate wound 6, the skin being already rendered sterile and having been shaved if necessary.

Figure 2:
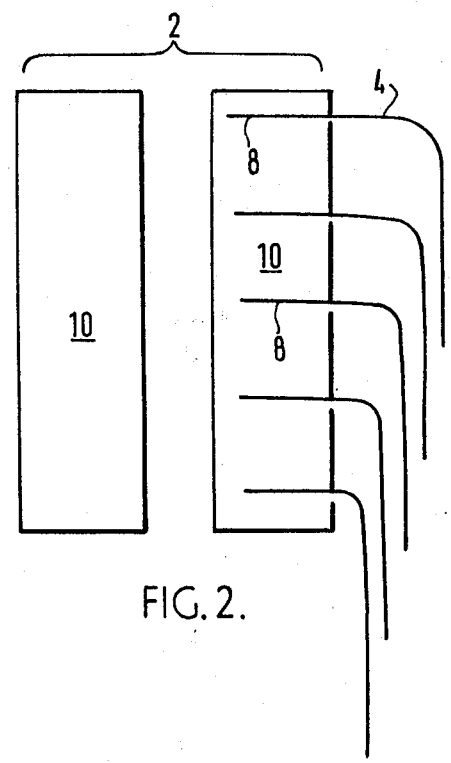
FIGS. 2 and 3 illustrate two possible forms of construction of the dressing.
Figure 3:
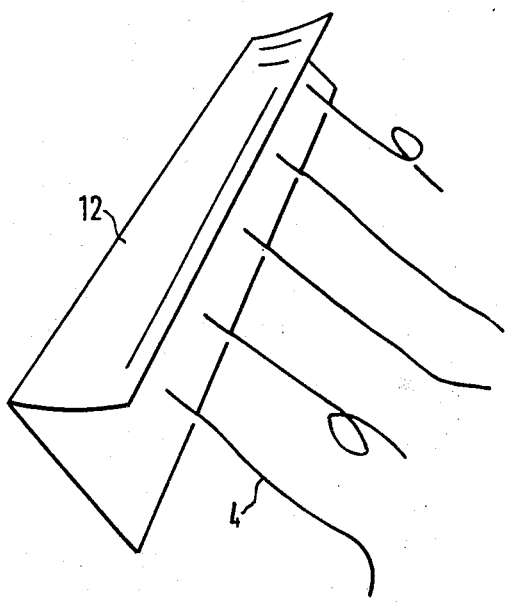
Figure 4:
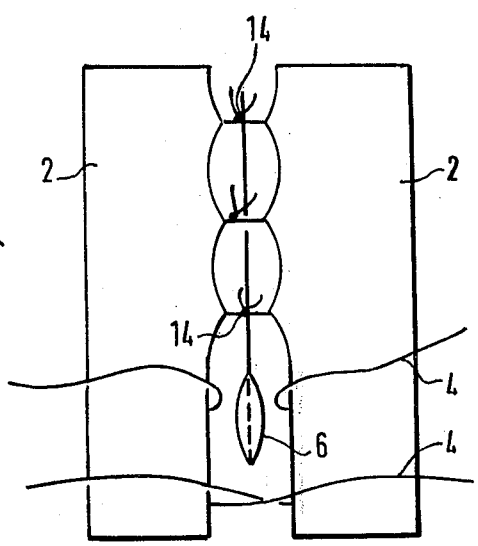
FIG. 4 illustrates an intermediate stage in the wound closure.

The fixing of the threads 4 to the strips must be strong and may be secured by trapping end portions 8 of the threads 4 between two superimposed strip portions 10 as shown in FIG. 2 or between a folded strip member 12 as shown in FIG. 3. The length of the threads 4 is approximately three times the width of the strips 2.

The threads 4 are then subjected to tension in turn by pulling one thread 4 from one strip 8 together with the corresponding thread from the opposite strip. When sufficient tension has been applied to close the wound edges together the threads are then tied in a firm knot 14. This action of pulling and tying is repeated with each succeeding pair of threads until the entire wound is closed.

Figure 5:
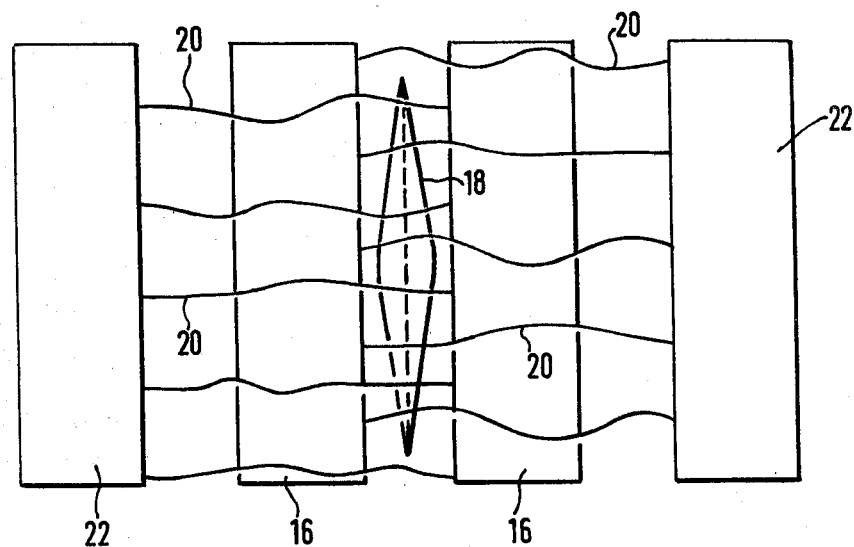
FIG. 5 diagrammatically illustrates a second example of the invention.

FIG. 5 shows the second example of the invention which comprises two first strips 16 which are arranged alongside but spaced from a wound 18 in a manner sim to that in which the strips 2 are placed in the first example. Threads 20 are provided, five for each strip 16; however, in this example the remote ends of the threads are not free, but are secured in one of two second strips 22. The length of each thread 20 is twice the width of the strips 16.

Figure 6:
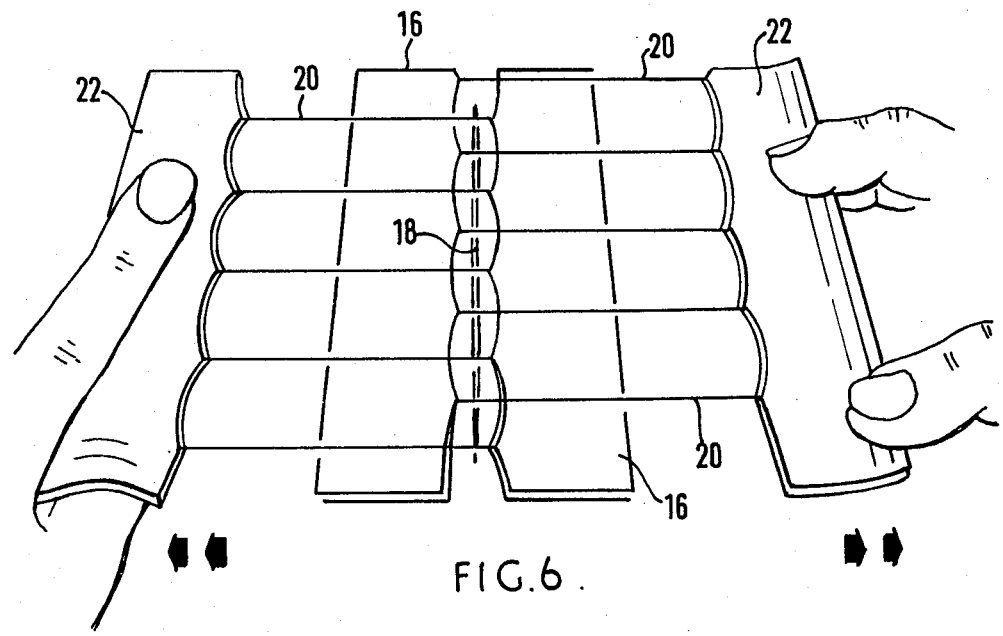
FIG. 6 shows an intermediate stage in the wound closure using the dressing shown in FIG. 5.

In applying the dressing, once the strips 16 have been positioned, the strips 22 will be grasped as shown in FIG. 6 so that tension is applied to the interlaced threads 20 by pulling in opposite directions. When sufficient tension has been produced to pull the edges of the wound 18 together, the strips 22 will be brought into contact with the patient's skin and caused to adhere firmly thereto. It will be appreciated that the length of the threads is selected such that there is no overlapping of the first and second strips, each thread from each strip 16 spanning the closed wound and completely traversing the strip 16 on the opposite side.

The manner in which the dressings achieve the desired action is illustrated in FIGS. 7 to 10.

Figures 7, 8:
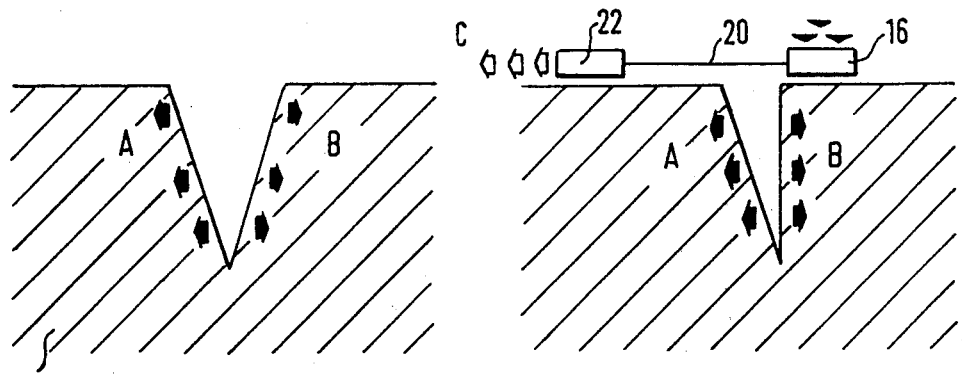
FIGS. 7–10 show in diagrammatic form the changes in stress pattern involved in using the second example of the invention.
Figure 9:
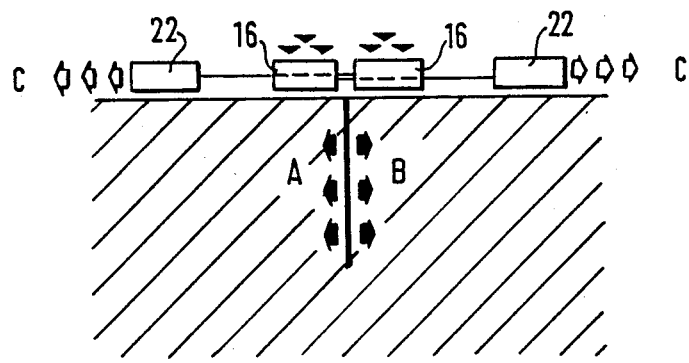
Figure 10:
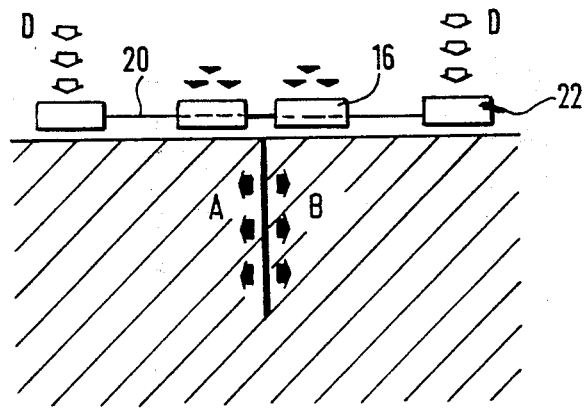

It will be understood that a wound tends to gape as shown in FIG. 7 because of tension forces A, B in the surrounding tissue 24. These forces must be matched by equal and opposite forces applied through the plaster strips and threads. Thus, in FIG. 8, for the sake of illustration, one strip 16 has been positioned adjacent the wound edge and a pulling force is being applied (arrows C) to the strip 22 to equal and overcome the force of tension at B. Similar pulling force on the other strip 22 (see FIG. 9) results in the wound being closed. The strips 22 are then pressed into place (D) to maintain the tension in the threads 20. Thus the adhesion strength of the strips 16, 22 must at least equal and preferably be greater than the tension forces A and B.

It will be understood that in practice pulling forces are exerted by both strips 22 at the same time, with individual variation and adjustment as deemed appropriate by the practitioner.

It is essential that the materials selected for the manufacture of the surgical dressing described herein are capable of sterilization by conventional methods such as ionising radiation and should be packed in a sealed sterile envelope.

Various modifications may be made within the scope of the invention as defined in the following claims.

I claim:

1. A surgical dressing for use to maintain elongate slit-type wounds of a patient's skin in a closed condition comprising:
   first and second strips of adhesive plaster each adapted to adhere to the patient's skin alongside but slightly spaced from lengthwise extending edges of the wound;
   a third strip of adhesive plaster having a plurality of filaments secured at spaced intervals along its length and coupled to said first strip;
   a fourth strip of adhesive plaster having a plurality of filaments secured at spaced intervals along its length, interlaced with the filaments of the first and third strips, and coupled to said second strip;
   wherein the length of each filament exceeds the width of the first or second strips so that the third and fourth strips may be adhered to the patient's skin at regions beyond the second and first strips, respectively, and each filament being adapted in use to co-operate under tension between one of said first and second adhesive strips and one of said third and fourth adhesive strips on the opposite side of the wound to draw the edges of the wound together.

2. A dressing as claimed in claim 1 wherein each strip is comprised of fabric and the end portions of the filaments are firmly embedded in the fabric of the strip.

3. A dressing as claimed in claim 1 or claim 2 wherein each strip has a coating of pressure-sensitive adhesive, and a removable protective layer which protects each strip prior to use.

* * * * *